United States Patent [19]
Schoenaich et al.

[11] 3,962,329
[45] June 8, 1976

[54] MANUFACTURE OF GRANULAR ISOBUTYLIDENEDIUREA

[75] Inventors: Guenther Schoenaich, Ludwigshafen; Otto Grabowsky, Limburgerhof; Johann Mayer; Guenther Matthias, both of Ludwigshafen, all of Germany

[73] Assignee: BASF Aktiengesellschaft, Ludwigshafen (Rhine), Germany

[22] Filed: Oct. 25, 1974

[21] Appl. No.: 517,889

[30] Foreign Application Priority Data
Nov. 5, 1973 Germany............................ 2355212

[52] U.S. Cl.............................. 260/553 R; 71/28; 71/37; 71/40; 71/41
[51] Int. Cl.².................. C07C 127/00; C05C 9/00; C05B 11/04

[58] Field of Search................................. 71/28–30, 71/37, 40, 41; 260/553 R, 555 R

[56] References Cited
UNITED STATES PATENTS

| | | | |
|---|---|---|---|
| 3,459,528 | 8/1969 | Wiesboeck et al. ..................... | 71/28 |
| 3,507,641 | 4/1970 | Richmond et al. ..................... | 71/37 |

*Primary Examiner*—Charles N. Hart
*Assistant Examiner*—Ferris H. Lander
*Attorney, Agent, or Firm*—Johnston, Keil, Thompson & Shurtleff

[57] ABSTRACT

The preparation of isobutylidenediurea from isobutyraldehyde and urea, the particle size of the product being controlled by alternate use of sulfuric acid and phosphoric acid.

5 Claims, No Drawings

MANUFACTURE OF GRANULAR ISOBUTYLIDENEDIUREA

The invention relates to a process by means of which isobutylidenediurea can be obtained in granular form, that is to say in a form with coarse particle size, during the actual manufacturing process.

Isobutylidenediurea (IBDU) is obtained by condensation of urea with isobutyraldehyde in solution or in bulk (compare German Patent No. 1,543,201) in the presence of mineral acids, in accordance with the equation

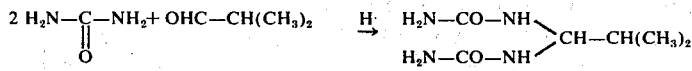

IBDU is used as a slow-acting nitrogenous fertilizer and as a source of nitrogen in the nutrition of ruminants, in place of urea (compare German Patent No. 1,146,080 and German Published Application No. 1,808,711).

It has already been disclosed that when the condensation is carried out in the absence of solvents (German Patent No. 1,543,201) IBDU is obtained in the form of a solid, the water produced by the condensation reaction being removed by drying. Solid IBDU can also be obtained from solutions.

When using IBDU as a slow-acting fertilizer, but also as a source of nitrogen in animal nutrition, it is desirable that the material should be in a coarse granular form; proposals for achieving this objective have already been made, as can be seen, for example, from British Patent No. 1,073,481. The proposals basically amount to adding auxiliaries, which act as binders, to the more or less pulverulent product.

Apart from the difficulty of carrying out these proposals industrially (as a rule, the binder is difficult to distribute in the powder uniformly and the formation of uniform particles proves difficult), such additives also entail increased expense and reduce the active ingredient content of the product.

The general information on methods of granulating pulverulent products, to be found, for example, in Ullmanns Encyklopädie der technischen Chemie (4th edition, volume 2, Process Technology I, Weinheim (1972)) also does not provide satisfactory solutions since additional process stages are required and these solutions are therefore economically unattractive; furthermore, these proposals as a rule also necessitate the use of auxiliaries.

We have now found that in the manufacture of IBDU by reaction of urea with isobutyraldehyde in the presence of mineral acids, granular isobutylidenediurea is obtained effortlessly from the condensation reaction if the latter is carried out in a specific way.

The solution of the problem rests on the observation that the use of phosphoric acid as the condensation catalyst causes the material already in granular form to grow into particles of constantly increasing size, whilst, in contrast, the use of sulfuric acid as the catalyst favors the production of a finely pulverulent reaction product.

Accordingly, the invention is that in the manufacture of isobutylidenediurea by condensation of urea and isobutyraldehyde in the presence of a mineral acid, phosphoric and sulfuric acid are used alternately as catalysts.

The process is not only applicable to cases where solid urea and isobutyraldehyde are used as the condensation agents, that is to say no solvent is used, but also where, for example, concentrated aqueous urea solutions are used. The process is even preferentially applicable when the starting materials are aqueous urea solutions containing approximately from 70 to 90% of urea.

With regard to the reaction conditions to be observed, the process does not differ inherently from the state of the art, that is to say the reaction is carried out at temperatures near the boiling point of isobutyraldehyde measured under normal pressure, that is to say from about 60°C up to about 100°C.

The amount of mineral acid used to achieve an adequate rate of condensation depends, inter alia, on the reaction temperature; in general, it is not more than approximately from 0.5 to 5 mole percent, based on urea. The ratio of phosphoric acid to sulfuric acid can be varied within a certain range; in general, approximately from 50 to 95% of phosphoric acid and approximately from 5 to 50% of sulfuric acid are used, but used alternately and not as a mixture. The time intervals in the alternate addition of phosphoric acid and sulfuric acid depend on the desired particle size and the spatial characteristics of the reaction vessel and are best determined by a preliminary experiment.

For example, the addition of phosphoric acid in each case lasts from 20 to 180 minutes and the addition of sulfuric acid from 2 minutes to 20 minutes. With this length of interval it is assumed that the requisite amount of mineral acid is approximately from 1.0 to 10 mole per cent, or from 2 to 20 equivalent per cent, based on the compound to be manufactured, and does not depend on the nature of the mineral acid.

The average residence time of the reaction product, which also has a certain influence on what are favorable intervals, is in general from 5 to 20 minutes. The average residence time can accordingly be significantly less than the addition interval, especially the addition interval for phosphoric acid. It is normally of advantage to introduce the condensation agent (sulfuric acid or phosphoric acid) into the reactor at a rate corresponding to that at which the reactants are introduced, that is to say also continuously.

High-speed mixers can be used with advantage as reaction chambers for carrying out the process according to the invention. Whilst stirred kettles are not unsuitable, they have the disadvantage that especially powders are difficult to discharge continuously or semicontinuously from such kettles; this is true in particular when, as in the present case, the powder first formed contains a certain amount of water which either has been introduced with the reactants or has been produced during the manufacturing process.

Particularly suitable types of mixers are, for example, centrifugal mixers and whirl mixers, with and without (partial) recycling.

According to experience gathered hitherto, mixers which have a horizontal stirrer shaft and which are operated so that the stirring elements have a peripheral speed of from 2.5 to 6 m/second are particularly advantageous to use for the process according to the invention. Suitable materials to use for the condensation in such equipment are, for example, aqueous urea solutions containing from 70 to 90% or more of urea, or solid urea. Of course, urea solutions of this concentration must be introduced not at room temperature, at which they would crystallize out, but warm. The reaction chambers preferably comprise means of preventing losses of isobutyraldehyde; isobutyraldehyde boils at about 60°C and is preferably recycled to the reaction chamber through a reflux condenser mounted on the mixer if, as is usual, the reaction temperature is from 60° to 100°C.

A process which has proved its value is the following:

Approximately 2 parts by weight of 75% strength aqueous urea solution, 1 part by weight of isobutyraldehyde, 0.1 part by weight of phosphoric acid (45% strength by weight) and 0.08 part by weight of sulfuric acid (75% strength by weight) are reacted continuously, by the method described below, in a reactor which consists of a fixed horizontal drum with a high-speed horizontal stirrer.

The urea solution is preheated to from 70° to 75°C in a heated vessel and fed to the reactor continuously by means of a pump. The pipelines to the reactor can also be heated. Isobutyraldeyde and phosphoric or sulfuric acid (which, according the the invention, are fed in alternately) are also each fed to the reactor by means of a pump.

The amount fed in is so chosen that the hourly throughput of product corresponds to from two to three times the volume of the reactor. However, the level in the reactor is kept sufficiently low to give an average residence time of 12 minutes or less.

A large, high-efficiency reflux condenser is mounted on the reactor; it condenses the isobutyraldehyde which vaporizes, and feeds it back into the reactor. Since the reaction is exothermic, a substantial proportion of the heat of reaction is removed in this way, that is to say through evaporative cooling. The temperature of the refluxing isobutyraldehyde affects the reaction temperature and should be so chosen that the temperature in the reaction mixture does not significantly exceed 100°C. At lower temperatures, the reaction of course proceeds more slowly, and excessively low temperatures should be avoided to prevent the granules from caking together to give larger aggregates.

The reaction product, which is already granular when leaving the reactor and which should, as far as possible, not contain more than from 1 to 6% of free urea, is next treated with alkali metal hydroxide solution to neutralize the mineral acid present. This of course produces a further amount of water but experience has shown that this water can be absorbed by the granules without causing caking. Thereafter, the granules are substantially freed from water in a suitable drier, and are thus stabilized.

EXAMPLE

A mixer of 600 liters capacity, with a horizontal stirrer shaft (speed of rotation $n$ = 110 revolutions per minute) is used; 458 liters of a urea solution which contains 854 g of urea per liter of solution are run in hourly. 320 liters of isobutyraldehyde and 18 liters of 45% strength phosphoric acid or 12 liters of 75 % strength sulfuric acid are added hourly. The phosphoric acid and sulfuric acid are added alternately, phosphoric acid being added for 50 minutes and sulfuric acid then being added for 10 minutes. The first mixer gives 773 kg of moist product per hour; this product is neutralized with 50% strength potassium hydroxide solution (18 liters per hour) in a second mixer, of 60 liters capacity. The product now contains about 25% of water, which is removed in a drier, down to a residual moisture content of 2%. 588 kg of granular product are obtained hourly. Particle size distribution:
 15% less than 0.25 mm
 35% from 0.25 mm to 0.7 mm
 30% from 0.7 mm to 1.25 mm
 15% from 1.25 mm to 2.0 mm
 5% more than 2.0 mm.

COMPARATIVE EXPERIMENT 1

Again, 458 liters of urea solution (854 g/lter), 320 liters of isobutyraldehyde and 12 liters of 75% strength sulfuric acid are reacted hourly in the equipment described in Example 1. After neutralization with approx. 18 liters of 50% strength potassium hydroxide solution, and drying, approximately 588 kg of a gritty product of the following particle size distribution are obtained:
 5% less than 0.1 mm
 35% from 0.1 mm to 0.25 mm
 35% from 0.25 mm to 0.5 mm
 15% from 0.5 mm to 0.7 mm
 10% more than 0.7 mm.

COMPARATIVE EXPERIMENT 2

Again, 458 liters of urea solution (854 g/liter) and 320 liters of isobutyraldehyde are fed hourly into the equipment described in Example 1. The catalyst used is a mixture of 90 parts by volume of 45% strength phosphoric acid and 10 parts by volume of 75% strength sulfuric acid. 17 liters of this mixture are fed hourly to the reactor. After neutralization with about 18 liters of 50% strength potassium hydroxide solution/hour, and drying, approximately 588 kg of a product which does not differ markedly from the particle size distribution of that in Comparative experiment 1 are obtained.

COMPARATIVE EXPERIMENT 3

If the procedure described above is followed but only phosphoric acid is used as the condensation agent, it does not prove possible to obtain a pulverulent material in the equipment described; instead, more or less coarse or lumpy aggregates are produced, which necessitate a shut-down of the equipment after a short time.

We claim:

1. In a continuous process for the production of solid granular isobutylidene diurea by condensation of urea with isobutyraldehyde in the presence of a mineral acid, catalyst, the improvement consisting of repeatedly alternately adding phosphoric and sulfuric acid at different intervals of time to the continuous feed of the urea and isobutyraldehyde.

2. A process as claimed in claim 1, wherein phosphoric acid and sulfuric acid are introduced alternately, phosphoric acid for a period of from 20 to 180 minutes and sulfuric acid for a period of from 2 to 20 minutes.

3. A process as claimed in claim 1 wherein the molar ratio of added phosphoric acid to added sulfuric acid is approximately 50:50 to 95:5.

4. A process as claimed in claim 3 wherein the amount of added mineral acid is maintained within a range of approximately 0.5 to 5 mole percent, based on the urea reactant.

5. A process as claimed in claim 3 wherein the average residence time in the condensation reaction is about 5 to 20 minutes.

* * * * *